(12) United States Patent
Zhang et al.

(10) Patent No.: US 7,542,794 B1
(45) Date of Patent: Jun. 2, 2009

(54) METHOD OF EXTRACTING AND EVALUATING PACED HEART BEATS USING MAX-MIN TRANSFORM ANALYSIS

(75) Inventors: Hongxuan Zhang, Hi-Nella, NJ (US); Ananth Natarajan, San Marino, CA (US); Nitish V. Thakor, Clarksville, MD (US)

(73) Assignee: Infinite Biomedical Technologies, LLC, Baltimore, MD (US)

( * ) Notice: Subject to any disclaimer, the term of this patent is extended or adjusted under 35 U.S.C. 154(b) by 350 days.

(21) Appl. No.: 11/439,900

(22) Filed: May 24, 2006

Related U.S. Application Data

(60) Provisional application No. 60/683,857, filed on May 24, 2005.

(51) Int. Cl.
*A61B 5/04* (2006.01)
(52) U.S. Cl. ............... 600/509; 600/510; 607/27
(58) Field of Classification Search .......... 600/509, 600/510, 515, 516, 521; 607/27, 28
See application file for complete search history.

(56) References Cited

U.S. PATENT DOCUMENTS

| | | | | |
|---|---|---|---|---|
| 3,940,692 A | * | 2/1976 | Neilson | 324/76.17 |
| 4,527,567 A | * | 7/1985 | Fischler et al. | 607/27 |
| 4,664,116 A | * | 5/1987 | Shaya et al. | 607/27 |
| 4,832,041 A | * | 5/1989 | Wang et al. | 600/510 |
| 5,682,902 A | * | 11/1997 | Herleikson | 600/521 |
| 5,771,898 A | * | 6/1998 | Marinello | 600/510 |
| 6,501,983 B1 | | 12/2002 | Natarajan et al. | 600/517 |
| 7,277,745 B2 | | 10/2007 | Natarajan et al. | 600/509 |
| 2003/0023176 A1 | * | 1/2003 | Yonce et al. | 600/510 |
| 2007/0129639 A1 | | 6/2007 | Zhang et al. | 600/509 |
| 2007/0244403 A1 | | 10/2007 | Nararajan et al. | 600/509 |

OTHER PUBLICATIONS

Jiapu Pan, and Willis Tompkins, "A Real Time QRS Detection Algorithm", IEEE Transaction on BME, vol. 32, No. 3, pp. 230-236, 1985.

\* cited by examiner

*Primary Examiner*—Carl H Layno
*Assistant Examiner*—Jennifer Stewart
(74) *Attorney, Agent, or Firm*—Konrad Raynes & Victor, LLP; Alan S. Raynes

(57) ABSTRACT

Methods for identifying and extracting heart depolarization and repolarization in a paced heart. Certain methods also include identifying and analyzing particular features of at least one pacing spike and QRS waveform for heart beat characterization. These features may include signal changing speed and signal time interval (distance) of pacing spikes and QRS depolarization when pacing excitation is initialized.

6 Claims, 6 Drawing Sheets

METHOD OF EXTRACTING AND EVALUATING PACED HEART BEATS USING MAX-MIN TRANSFORM ANALYSIS

This application claims priority to U.S. Provisional Application No. 60/683,857, filed on May 24, 2005, which is hereby incorporated by reference in its entirety.

RELATED ART

ECG (electrocardiogram) signal features such as heart depolarization (QRS complex) and repolarization (ST segment) are susceptible to signal changes. Although these changes are sensitive to artifacts and noise, such as muscle and body movements, they provide a window into the heart's condition. Accurate identification and extraction of the paced heart beat are significant for monitoring and cardiac rhythm analysis and evaluation, especially for implantable devices, including pacemakers and defibrillators. Hence development of identification strategies for paced heart beats will be helpful for clinical doctors and cardiac patients.

DESCRIPTION OF EMBODIMENTS

Figure 1:
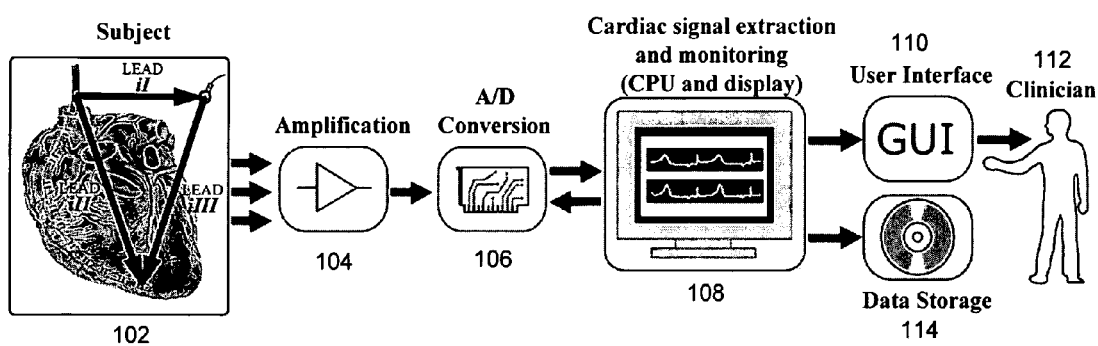
FIG. 1 illustrates a system of paced heart monitoring, analysis, storage and display in accordance with certain embodiments.

Certain embodiments relate to the methods and approaches for identification and extraction of the depolarization and repolarization in a paced heart. Certain preferred embodiments pertain to the technologies of characterizing heart beats in both paced and nonpaced rhythm during the cardiac monitoring and analysis. The strategies in certain preferred embodiments may also be utilized in internal lead systems (e.g. myocardial lead sensors) as well as external lead systems (e.g. surface ECG recording).

Certain embodiments relate to the methods and algorithms of identifying particular features of the pacing spikes and QRS waveform for heart beat characterization. These features include signal changing speed and signal time interval (distance) of pacing spikes and QRS depolarization when pacing excitation is initialized. Nonpaced heart beat, premature heart beat, fusion heart beat, and other related artifacts and cardiac arrhythmia, may cause inaccurate paced heart beat characterization. Certain preferred embodiments of the invention may further comprise threshold and saturation analysis for discriminating appropriate heart beats from the mentioned noise contamination and distortion.

Embodiments may also include modified approaches and methods for heart beat characterization, such as multi-beat averaging and adaptive threshold based beat extraction, continuously or periodically. Certain preferred embodiments may further include paced heart beat identification which is based on modified nonpaced heart beat extraction, such as algorithms with pacing spike cancellation.

Certain embodiments may find application in both implantable devices, such as pacemakers and defibrillators, and external heart monitoring platforms.

Certain embodiments may relate to a signal processing algorithms and analysis for paced heart beat identification, extraction and characterization.

Certain embodiments include feature analysis and extraction of the pacing heart beats which could be utilized to characterize the paced heart beat in both continuously and periodically monitoring cases. Further, the method of discriminating successful paced heart beat from noise contamination and distortion is based on signal changing speed (by differentiation of signal) and time distance analysis. In addition, certain embodiments can be very useful in complex paced heart monitoring, such as VOO (fixed rate asynchronous pacing in the ventricle. There could be unsuccessful heart pacing or fusion beats in the VOO pacing mode.), and VVI (sensing circuits were developed to permit inhibited modes of pacing. There could be nonpaced heart beats in the VVI pacing mode.). The technology for identifying paced heart beat in certain embodiments of certain embodiments may be utilized in implantable devices for reliable, accurate and real time cardiac monitoring.

These features of certain methods can be more fully understood from the following description, which can be read in light of the accompanying drawings.

FIG. 1 shows aspects of a cardiac monitoring system in accordance with certain embodiments. A cardiac signal can be extracted from cardiac subject 102. Although the cardiac subject 102 shows an internal tri-angle lead system iI, iII, and iIII, heart signals could as well be extracted from external leads, or from cardiac lead systems other than the internal tri-angle leads iI, iII, and iIII illustrated in FIG. 1. Module 104 is an amplifier function head box for cardiac signal tuning, adjusting and filtering. Module 106 is for cardiac signal digitization and acquisition and includes an analog to digital converter. Module 108 performs cardiac heart beat extraction and may include a CPU (central processing unit), a monitoring display, and code for carrying out various operations. The module 108 is capable of selecting the pacing spike and rejecting the unsuccessful pacing heart beats in the real time cardiac monitoring and processing. The output of module 108 may be used for several purposes. For example, it may be used by an implantable device, such as pacemaker, to identify an appropriate beat for morphological analysis or time-frequency analysis. Alternatively, optional function 110 is a versatile interface such as a graphical user interface (GUI) for monitoring, analysis and interpretation by a clinician 112. The module 110 may be utilized for signal display, graphic interface or related analysis parameters via a wired or wireless link. Module 114 is for data storage.

Figure 2:
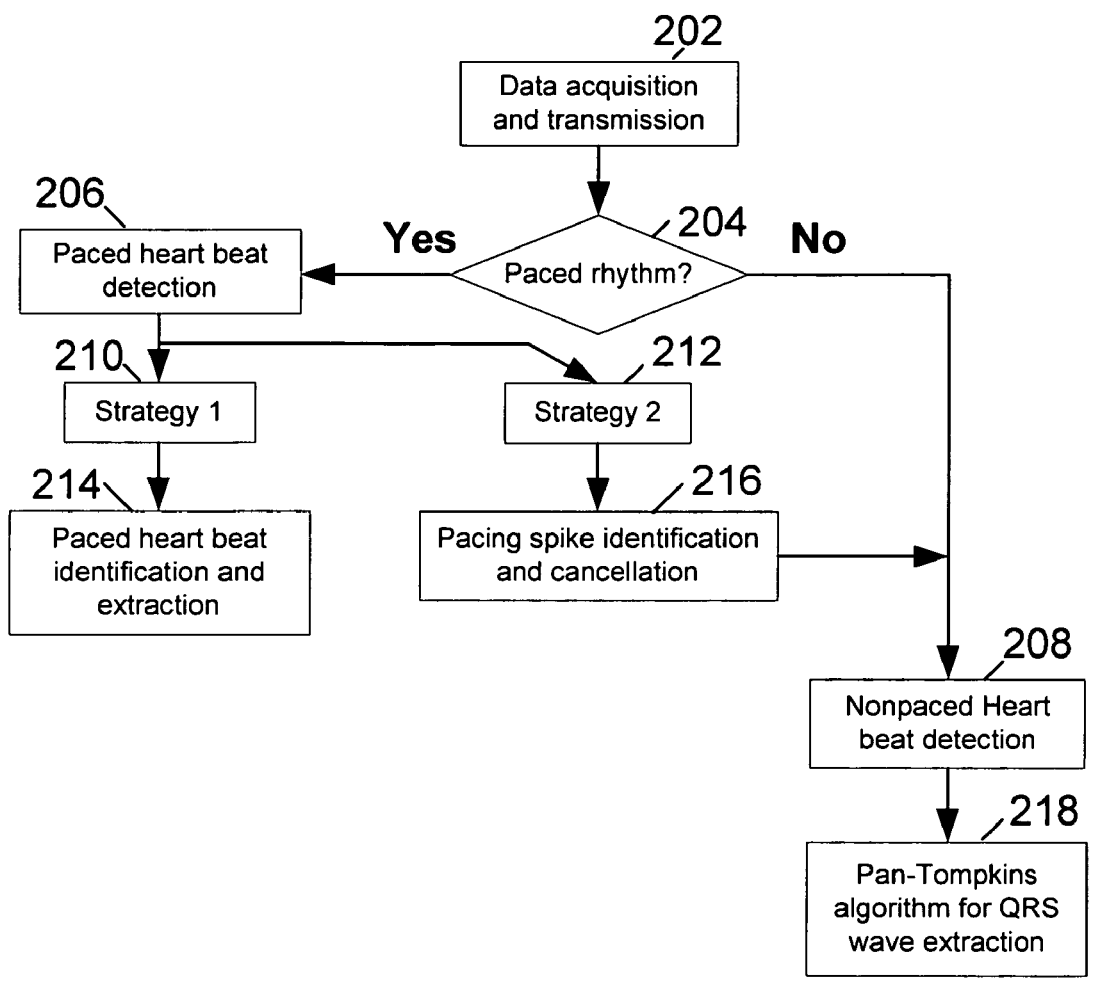
FIG. 2 illustrates a flow chart including strategies for paced heart beat analysis and identification in accordance with certain embodiments.

FIG. 2 illustrates a flow chart that identifies methods and strategies for paced heart beat analysis and identification in accordance with certain embodiments. Compared with approaches for nonpaced heart beat analysis, the identification and characterization of the paced heart beat are generally more complex.

In FIG. 2, block 202 is for paced heart beat signal acquisition and transmission. Block 204 is an analysis module to decide whether the acquired signals are in paced heart beat rhythm or not. In block 204, additional information may be also included, such as the pacing rate, pacing mode (e.g. VOO and VVI), pacing pulse duration and pacing/signal acquisition position. These parameters and pre-knowledge (e.g. VOO, VVI) are generally used in the identification of the pacing heart beats. If the cardiac signal is in pacing rhythm, block 206 will start analyzing the acquired cardiac signals. Otherwise, block 208 will be utilized to characterize the nonpaced heart beat information. If they are paced heart beat signals, certain embodiments include two approaches for paced heart beat identification as previously mentioned, strategy 1 (block 210) and strategy 2 (block 212). Strategy 1 is for paced heart beat identification and extraction, with detailed operations described in FIG. 3. Strategy 2 is for pacing spike identification and cancellation. Block 216 utilizes pacing spike cancellation as an approach for paced heart beat identification. This approach can extract out the pacing spikes based on pre-knowledge, such as pacing heart rate and mode. Then compared with acquired cardiac pacing signals, the pacing spikes inside can be subtracted and cancelled. The paced heart beat signal after pacing spike cancellation is just like a nonpaced signal, especially the QRS depolarization. Hence, nonpaced heart beat extraction strategies 208 can be applied to strategy 2 in the paced heart beat extraction. Block 218 is a reliable R wave detection approach for nonpaced cardiac signals, for example, the known Pan-Tompkins algorithm (see Jiapu Pan, and Willis Tompkins, "A Real Time QRS Detection Algorithm", IEEE Transaction on BME, Vol. 32, No. 3, pp. 230-236, 1985, which is hereby incorporated by reference in its entirety). Other known detection approaches for the detection and analysis of heartbeats including, but not limited to, the QRS complex, for nonpaced cardiac signals, may also be used. In certain embodiments, the application of nonpaced heart beat extraction and analysis into modified paced heart beat signal is also useful in the VOO pacing mode. Certain embodiments include performing QRS depolarization analysis of a non-paced signal.

Figure 3:
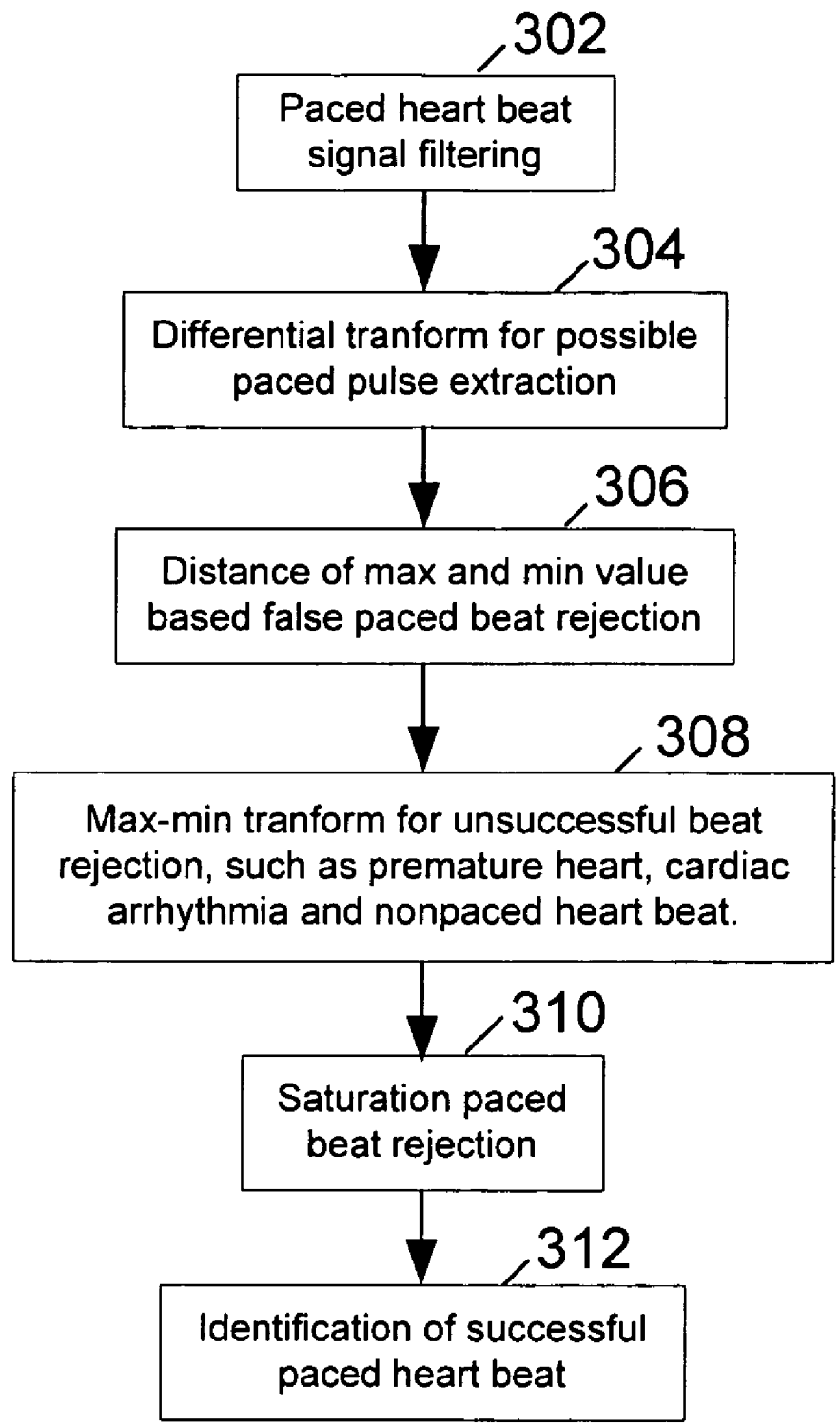
FIG. 3 illustrates a flow chart for paced heart beat testing and evaluation, in accordance with certain embodiments.

However, there are numerous pacing heart modes, such as VVI, VOO and other cardiac pacing methods, in which the paced heart beats are difficult to be extracted via the modified signal as in the strategy 2 in FIG. 2. Additionally, bio-noise, such as muscle and body movement, and other related noise, can decrease the raw signal to noise ratio and distort the heart beat signals. Hence, certain embodiments of the present invention may also include more accurate and reliable algorithms for paced heart beat identification and extraction. FIG. 3 shows a schematic flowchart for paced heart beat extraction and analysis in strategy 1 in FIG. 2, in accordance with certain embodiments.

Block 302 is for paced heart beat tuning and signal filtering. This process can decrease the contamination and distortion from environmental noise and bio-noise, such as respiration shifting and big artifact signal rejection. Blocks 304 to 310 are operations for the max-min (maximum-minimum) analysis for paced heart beat identification. Block 304 is a function module for differential transform of any possible pacing pulse extraction. Differential transform can extract the signal changing trend. In the differential signals, the pacing spike and QRS depolarization should have the highest signal changing speed, which can be utilized to characterize the time position of the pacing pulse and QRS wave. Via raw cardiac signal analysis of the cardiac recording data, max and min values of the raw signal can be derived. Through time distance analysis of max and min values (e.g., the time distance between pacing spike and R wave should not be smaller than 50 ms or bigger than 150 ms when the pacing heart rate is 100 per minute, for example), block 306 can reject the false paced beats, such as non-paced beats and fusion beats. Block 308 is a further signal process of max-min transform for rejecting unsuccessful heart beats. Through the analysis of max-min transform, the premature beats, arrhythmic heart beat and nonpaced heart beats can be precisely and reliably removed from the cardiac signals. The Kernel mechanism of the max-min theories as used in certain embodiments is described below.

In certain embodiments, heart beat rejection methodology can be achieved via developing a max-min rejection approach for paced heart beats in which the distance between biggest value point (R wave) and smallest value point (Q or S wave) of the original paced signal should not bigger than a threshold, such as, for example, 60 ms (dependent on data digitizing frequency.). The Max-Min test and analysis are useful for both original signal and differential signal. In the differential signal, there should be two local maximum: the pacing spike and the R-wave. The pacing spike should precede the R-wave or the heart beat should be rejected. The local minimum value of each paced beat after the pacing spike should be either the Q or the S wave. Via the minimum test, the distance $D_{QRS}$ from Q to R and from R to S wave can be characterized:

$$D_{QRS}=\max(\text{distance}(QR),\text{distance}(RS)).$$

So the distance $D_{R\text{-}pace}$ between R wave and pacing spike can be obtained from raw cardiac signals. If $D_{R\text{-}pace}$ is smaller than $D_{QRS}$, then we can reject the beat as a false paced heart beat.

After distance and max-min test and analysis, module 310 is utilized to reject the saturation paced heart beats. The saturation of QRS complex signal can be caused by some kind of physiological changes or patient movement (artifacts and noise), pacing heart beats with this kind of noise and contaminations also need to be removed. In module 312, the successful paced heart beat can be derived at last. In certain preferred embodiments, threshold test and analysis for both raw and differential cardiac signals, such as max-min value selection and unsuccessful beat rejection from noise contamination.

Example One

Figure 4:
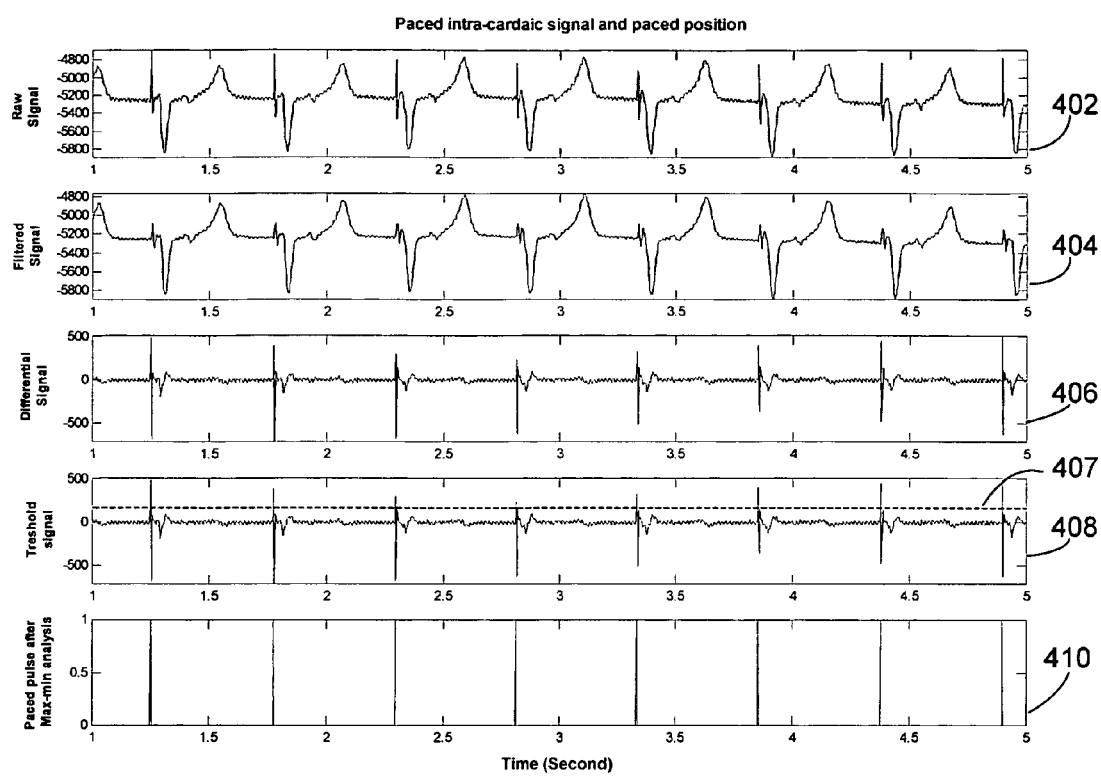
FIG. 4 illustrates the output during various operations relating to paced heart beat identification, in accordance with certain embodiments.

This example is to demonstrate a working sequence strategy in accordance with certain embodiments. FIG. 4 shows the step results of the paced heart identification and extraction. In the figure, plot 402 shows the raw cardiac paced signal with raw signal high-frequency signal fluctuation and noise. Plot 404 shows the cardiac signal after band pass signal filtering (0-80 Hz), artifact rejection, and signal range tuning. Plot 406 is the differential signal of the raw cardiac data. It is obvious in the differential cardiac signal that a pacing spike has a higher signal changing speed. This feature can be utilized to characterize the max and min value for the signal test and analysis. Plot 407 is signal threshold for max and min value test. This threshold can be adjusted to test multiple max and min values in the signals, such as ±1.6 multiplied by the mean value of cardiac signal. Based on the threshold test and analysis, the time position of the pacing spikes and QRS depolarization can be achieved in plot 408. Then, max-min transform analysis can be utilized to remove the premature heart beats, fusion beats and other unsuccessful heart beats in the pacing rhythm. Plot 410 shows the final pacing pulse position.

Example Two

Figure 5:
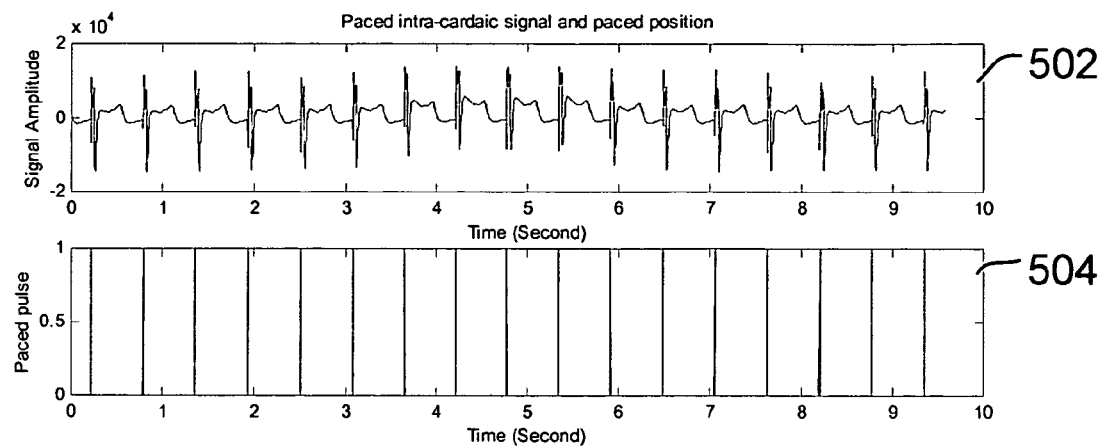
FIG. 5(a)-(d) illustrate output including examples of paced heart beat extraction in different noise and artifact situations, in accordance with certain embodiments.
Figure 5:
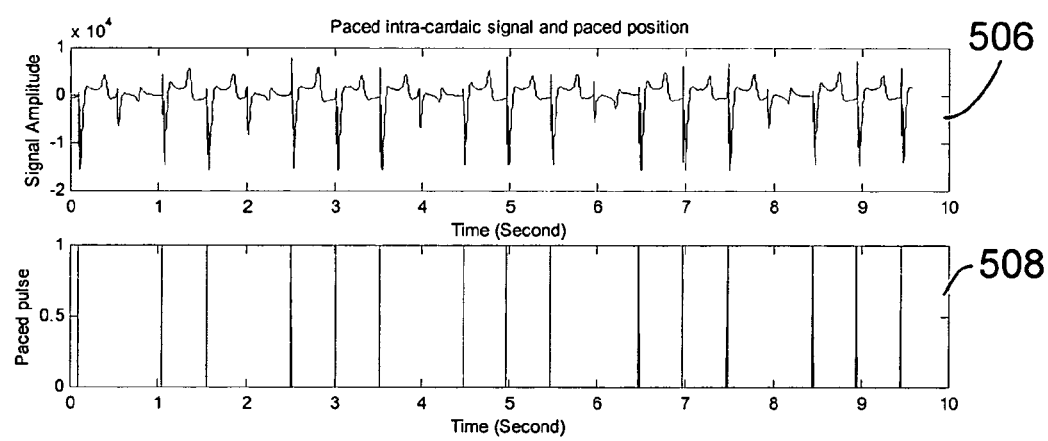
Figure 5:
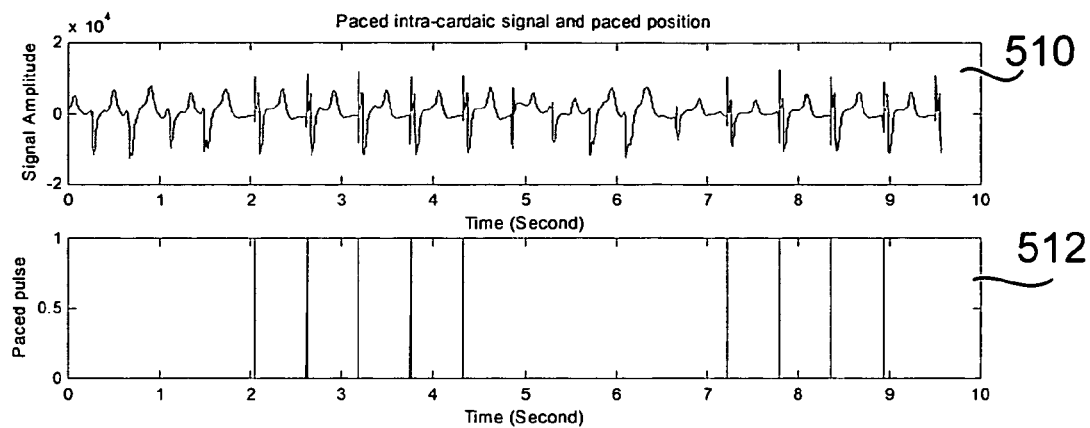
Figure 5:
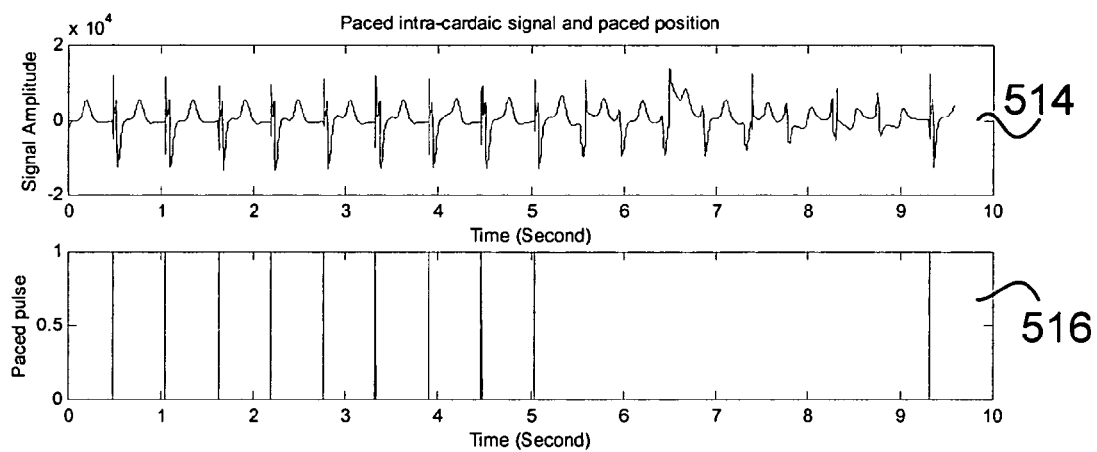

This example is to show results in different situations, such as cardiac arrhythmia and other noisy situations in the pacing heart beat extraction, in accordance with certain embodiments. FIG. 5 (a) relates to detecting normal paced heart beats. Under "normal" conditions, the pacing pulse initiates the start of the heart beat, and the FIG. 5 (a) plots illustrate detection during an uncomplicated ventricular pacing rhythm. The top plot 502 in FIG. 5 (a) shows a normal series of paced beats, while the bottom plot 504 in FIG. 5 (a) shows our ability to detect the normal beat (rising edge indicating the presence of a normal beat). FIG. 5 (b) relates to discriminating paced beats from non-paced beats. Non-paced beats may be encountered for example, during VVI pacing. However, the QRS complex (depolarization) in these cases will be very different than the paced depolarization complex, and is generally not appropriate for comparison. In FIG. 5 (b), the top plot 506 shows an ECG containing both paced and non-paced beats. The lower plot 508 of FIG. 5 (b) shows a beat selection approach, which rejects non-paced signals and fusion signals. FIG. 5(c) relates to discriminating paced beats from an arrhythmia. Under some conditions, a native arrhythmia may drive the heart beat. Similar to the above case, all of these beats are not suitable for comparison. FIG. 5 (c) illustrates the performance of paced beat detection during an arrhythmia (in this case there is ventricular tachycardia and then a short run of PVCs). In FIG. 5 (c), the top plot 510, shows an ECG during an arrhythmia, such that the resulting artifact corrupts the paced waveform. In the bottom plot 512 of FIG. 5 (c), normal and successful paced heart beats are extracted out from the complex and noise raw signals. FIG. 5 (d) relates to detecting paced beats in a complex environment. According to the examples and description, in a real pacing heart beat, there may exist nonpaced beats, fusion beats and arrhythmias. Our approach operations successfully identify paced depolarizations and extracts their respective QRS complexes. FIG. 5 (c) demonstrates this embodiment's performance in such a complex environment. In FIG. 5 (d), the top plot 514 shows an ECG that contains paced beats, non paced beats, fusion beats, and an arrhythmia. The approaches in accordance with certain embodiments have the ability to pick out the successful paced beats (see FIG. 5 (d) bottom plot 516).

It is, of course, understood that modification of the present embodiments of the invention, in its various aspects, will be apparent to those skilled in the art. Additional method and device embodiments are possible, their specific features depending upon the particular application.

The invention claimed is:

1. A method of analyzing paced heart beats, comprising:
providing a paced ECG signal including at least one QRS depolarization region and at least one pacing spike;
analyzing the at least one QRS depolarization region and the at least one pacing spike using max-min transform analysis of the ECG signal; and
identifying a time position of the at least one pacing spike in the paced ECG signal based on the max-min transform analysis of the ECG signal
wherein the max-min transform analysis of the ECG signal includes:
a first distance value between one of the at least one pacing spikes and an R-wave of the QRS depolarization region;
a second distance value between a Q-wave portion of the QRS depolarization region and the R-wave portion of the QRS depolarization region;
a third distance value between the R-wave portion of the QRS depolarization region and an S-wave portion of the QRS depolarization region; and
comparing the first distance value to the greater of the second and third distance values, and if the first distance value is smaller, then identifying the signal as a false paced heart beat.

2. The method of claim 1, wherein the paced ECG signal is selected from the group consisting of a raw ECG signal and a differential ECG signal.

3. The method of claim 1, further comprising performing a differential transformation of the paced ECG signal prior to the analyzing.

4. The method of claim 1, wherein the paced ECG signal is selected from the group consisting of an internal cardiac signal and a body surface cardiac signal.

5. The method of claim 1, further comprising, after identifying the time position, removing the at least one pacing spike from the paced ECG signal to yield a non-paced signal.

6. The method of claim 5, further comprising performing QRS depolarization analysis of the non-paced signal.

* * * * *